United States Patent [19]

Nishida et al.

[11] Patent Number: 5,260,457

[45] Date of Patent: Nov. 9, 1993

[54] PROCESS FOR PRODUCING COUMARIN AND DERIVATIVE THEREOF

[75] Inventors: Yoshitaka Nishida; Tamio Shirafuji; Kiyomi Sakai; Kensen Okusako, all of Ehime, Japan

[73] Assignee: Sumitomo Chemical Co., Ltd., Osaka, Japan

[21] Appl. No.: 921,747

[22] Filed: Jul. 30, 1992

[30] Foreign Application Priority Data

Jul. 31, 1991 [JP] Japan .................. 3-191400

[51] Int. Cl.$^5$ .................. C07D 311/14; C07D 311/16
[52] U.S. Cl. .................. 549/290
[58] Field of Search .................. 549/290

[56] References Cited

U.S. PATENT DOCUMENTS 3,442,910 5/1969 Thweatt .................. 260/343.2

FOREIGN PATENT DOCUMENTS 1349638 4/1974 United Kingdom .
1390307 4/1975 United Kingdom .

OTHER PUBLICATIONS

Patent Abstracts of Japan, vol. 15, No. 461 (C-887), Nov. 22, 1991.

Primary Examiner—C. Warren Ivy
Assistant Examiner—Ba K. Trinh
Attorney, Agent, or Firm—Sughrue, Mion, Zinn, Macpeak & Seas

[57] ABSTRACT

A process for producing coumarin and a derivative thereof represented by formula (2):

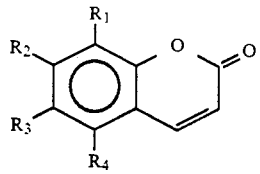

wherein $R_1$ to $R_4$ each represents a hydrogen atom, a methyl group, or an ethyl group, provided that at least two of $R_1$ to $R_4$ each represents a hydrogen atom, the process comprising the step of heating a 3-(2-cyclohexanoyl)propionic acid ester represented by formula (1):

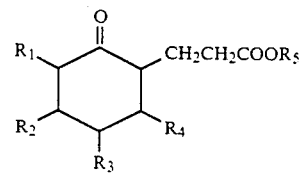

wherein $R_1$ to $R_4$ are as defined above and $R_5$ represents an alkyl group having from 1 to 4 carbon atoms, in the presence of a palladium catalyst, thereby to allow the ester of formula (1) to undergo cyclization and dehydrogenation reactions, the latter stage of the reactions, in which the conversion of the 3-(2-cyclohexanoyl) propionic acid ester used as a starting material has reached about 80% or more, being conducted at a higher temperature than that for the former stage of the reactions.

5 Claims, No Drawings

PROCESS FOR PRODUCING COUMARIN AND DERIVATIVE THEREOF

FIELD OF THE INVENTION

The present invention relates to an improvement in a process for producing coumarin and a derivative thereof from 3-(2-cyclohexanoyl)propionic acid esters. Coumarin and its derivatives, along with 3,4-dihydrocoumarin and its derivatives, are important compounds particularly in the perfume industry and can also be important intermediates for agricultural chemicals, drugs, and dyes.

BACKGROUND OF THE INVENTION

Conventionally known methods for producing coumarin and its derivatives include, for example, a process in which a 3-(2-cyclohexanoyl)propionic acid ester is heated in the presence of a hydrogenation-dehydrogenation catalyst, such as a palladium catalyst, thereby to allow the ester to undergo cyclization and dehydrogenation (as described in U.S. Pat. No. 3,442,910); and a process in which the cyclization and dehydrogenation reactions for producing coumarin and its derivatives are performed in the presence of both a noble metal catalyst such as a palladium catalyst and a promoter such as barium sulfate or nickel oxide (as described in JP-A-60-181082). (The term "JP-A" as used herein means an "unexamined published Japanese patent application.")

However, the conventional processes have been defective in that the yields of coumarin and its derivatives are not always high. In addition, there has been a problem that when the reaction is conducted under severe conditions in the initial stage thereof, the conversion of the 3-(2-cyclohexanoyl)propionic acid ester used as a starting material is low. If the reaction mixture resulting from the cyclization and dehydrogenation reactions contain the 3-(2-cyclohexanoyl)propionic acid ester, the ester comes into a final product to be obtained from the reaction mixture because removal thereof by purification is difficult, and the contaminant in the final product can be a cause of offensive odor.

SUMMARY OF THE INVENTION

An object of the present invention is to provide an improved process for producing coumarin and a derivative thereof, in which the conversion of the starting 3-(2-cyclohexanoyl)propionic acid ester is heightened and at the same time, the yield of coumarin is also heightened.

Other objects and effects of the present invention will be apparent from the following description.

The present inventors have conducted intensive studies in order to develop a process for producing coumarin and a derivative thereof in good yields and at low cost. As a result, it has been found that the yields of coumarin and a derivative thereof are improved greatly and the conversion of a starting 3-(2-cyclohexanoyl)propionic acid ester is also improved, when the former stage of the cyclization and dehydrogenation reactions is conducted at a relatively low temperature and low stirring power, and the latter stage of the reactions is conducted at a higher temperature and/or higher stirring power. The present invention has been completed based on this finding.

The present invention provides a process for producing coumarin and a derivative thereof represented by formula (2):

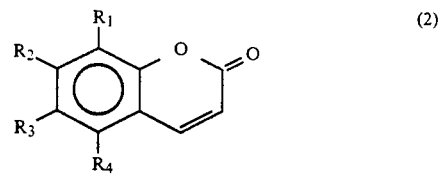

wherein $R_1$ to $R_4$ each represents a hydrogen atom, a methyl group, or an ethyl group, provided that at least two of $R_1$ to $R_4$ each represents a hydrogen atom, said process comprising heating a 3-(2-cyclohexanoyl)propionic acid ester represented by formula (1):

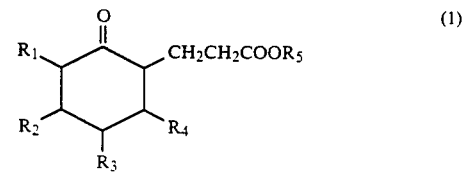

wherein $R_1$ to $R_4$ are as defined above and $R_5$ represents an alkyl group having from 1 to 4 carbon atoms, in the presence of a palladium catalyst, thereby to allow the ester of formula (1) to undergo cyclization and dehydrogenation reactions, in which the latter stage of the reactions, in which the conversion of the 3-(2-cyclohexanoyl)propionic acid ester used as a starting material has reached about 80% or more, is conducted at a higher temperature than that for the former stage of the reactions.

DETAILED DESCRIPTION OF THE INVENTION

Examples of the 3-(2-cyclohexanoyl)propionic acid ester represented by formula (1) used in the process of the present invention include
methyl 3-(2-cyclohexanoyl)propionate,
butyl 3-(2-cyclohexanoyl)propionate,
methyl 3-(3-methyl-2-cyclohexanoyl)propionate,
methyl 3-(5-methyl-2-cyclohexanoyl)propionate,
propyl 3-(4-ethyl-2-cyclohexanoyl)propionate,
propyl 3-(3,4-diethyl-2-cyclohexanoyl)propionate,
propyl 3-(3,4-dimethyl-2-cyclohexanoyl)propionate,
methyl 3-(3,5-diethyl-2-cyclohexanoyl)propionate, and
methyl 3-(3-ethyl-6-methyl-2-cyclohexanoyl)propionate.

Among these, methyl 3-(2-cyclohexanoyl)propionate is preferably used. However, the compound of formula (1) is not limited to these examples.

The catalyst used in the process of the present invention may be a heterogeneous metal catalyst which comprises palladium supported on a carrier made of at least one member selected from the group consisting of Groups IIA, IIIA, IVA, and VIA elements of the periodic table and compounds of these elements, such as carbon, alumina, silica gel, and barium sulfate. Such catalysts may be prepared by known methods, for example, by the impregnation-fixation technique (as described, e.g., in *Shokubai Chosei Kagaku* (Chemistry of Catalyst Preparation), edited by S. Ozaki, published by Kodansha, Japan) in which a carrier is impregnated with the metal and the resulting mixture is subjected to hydrogen reduction at a high temperature. Commercially available catalyst may also be used as it is.

The catalyst is generally used in an amount of about from 0.1 to 5% by weight, preferably about from 0.3 to 2% by weight, based on the amount of the 3-(2-cyclohexanoyl)propionic acid ester used. If the amount of the catalyst is too small, the reactivity tends to become too low, whereas it is too large, not only the reactivity tends to become too high and, hence, an increased amount of by-products forms but also the cost for the catalyst increases.

In the present invention, the term "latter stage of the reactions" used herein means a part of the reactions in which the conversion of the 3-(2-cyclohexanoyl)propionic acid ester used as a starting material has reached about 80% or more, and the term "former stage of the reactions" used herein means a part of the reactions in which the conversion of the 3-(2-cyclohexanoyl)propionic acid ester used as a starting material has not yet reached about 80%. Although the time when the reactions enter into its latter stage varies depending on the reaction temperature and other factors, the latter stage of the reactions generally begins about 7 to 15 hours after the initiation of the reactions. The latter stage of the reactions is conducted at a higher temperature than the former stage thereof.

The temperature for the cyclization and dehydrogenation reactions of the 3-(2-cyclohexanoyl)propionic acid ester is generally in the range of about from 100° to 350° C., preferably about from 230° to 295° C. In order to allow the starting 3-(2-cyclohexanoyl)propionic acid ester to react sufficiently and to increase the conversion thereof, it is preferred to conduct the former stage of the reactions at a temperature of about from 230° to 260° C. It is preferable that the reaction temperature is then raised and the latter stage of the reactions is conducted at a temperature higher by about from 20° to 40° C. than the temperature for the former stage of the reactions, in order to improve the yields of coumarin and a derivative thereof. It is not preferred that the reactions are conducted at a high temperature in its all stages, because this results in an insufficient conversion.

The rate of increasing the temperature is not particularly limited, and in general, the temperature is increased by about from 20° to 40° C. over about from 0.5 to 2 hours. Although the temperature may start to be increased before reaching the latter stage and may be gradually increased, it is preferred that the temperature is increased substantially after reaching the latter stage.

Stirring of the reaction system during reactions may generally be effected at a stirring power of about from 0.01 to 3 kW/m$^3$, preferably about from 0.05 to 1.5 kW/m$^3$, since too low a stirring power tends to result in a low coumarin yield, while too high a stirring power does not bring about a sufficient conversion. Although the reaction system is kept being stirred at a stirring power as high as from 1 to 3 kW/m$^3$ in its all stages, it is preferred that the former stage of the reactions is conducted while the reaction system is kept being stirred at a stirring power of about from 0.05 to 0.5 kW/m$^3$ in order to sufficiently react the raw-material 3-(2-cyclohexanoyl)propionic acid ester and to thereby attain an improved conversion, and the latter stage of the reactions is conducted while the reaction system is kept being stirred at a stirring power higher by about from 1 to 1.5 kW/m$^3$ than that for the former stage in order to improve the yields of coumarin and a derivative thereof.

The stirring power may be gradually increased over about from 0.5 to 1 hour, but in general, the stirring power is increased at once after reaching the latter stage.

A solvent may be used for performing the cyclization and dehydrogenation reactions. Examples of the solvent include phenyl ether, benzyl ether, methyl α-naphthyl ether, ethylnaphthalene, dimethylbiphenyl, dodecane, tetradecane, tetralin, acetophenone, phenyl propyl ketone, methyl benzoate, and dimethyl glutamate. The amount of the solvent is generally from 0.5 to 10 times by weight the amount of 3-(2-cyclohexanoyl)-propionic acid ester.

The cyclization and dehydrogenation reactions can be carried out by charging a 3-(2-cyclohexanoyl)propionic acid ester of formula (1) and a palladium catalyst in a reaction vessel along with a solvent if required, and then heating the reaction mixture for a period of from several hours to several tens of hours. As a result of the reactions, 3,4-dihydrocoumarin or its derivative can be obtained in a yield of about from 30 to 45% and coumarin or its derivative can be obtained in a yield of about from 20 to 40%. Besides these compounds, o-ethylphenol, dihydrocinnamic acid esters, octahydrocoumarin and the likes are formed as by-products. The reaction mixture is washed with an alkali, if required, and is then subjected to rectification, thereby to obtain coumarin and its derivative(s). 3,4-Dihydrocoumarin may be marketed as it is, or may be converted to coumarin through dehydrogenation.

The reaction vessel used for the cyclization and dehydrogenation reactions is not particularly limited, and a batch reactor having a stirrer is generally used.

If the conversion of the 3-(2-cyclohexanoyl)propionic acid ester is low and part of the ester remains in the reaction mixture, the remaining ester is apt to come into purified products to be obtained from the reaction mixture, especially into 3,4-dihydrocoumarin and its derivative(s) because the ester is difficult to remove by purification. Since the ester becomes a cause of offensive odor, it is advantageous that the conversion of the 3-(2-cyclohexanoyl)propionic acid ester is regulated at about 99.5% or higher, preferably 99.9% or higher, more preferably 99.95% or higher. This can be attained by the process of the present invention.

According to the process of the present invention, the conversion of the starting 3-(2-cyclohexanoyl)propionic acid ester can be heightened, and therefore, the problem of offensive odor due to inclusion of the starting material into final products can be eliminated. At the same time, coumarin can also be produced in a heightened yield.

The present invention will be explained below in more detail with reference to the following examples, which should not be construed to be limiting the scope of the invention.

EXAMPLE 1

In a 1-liter four-necked flask, 300 g of methyl 3-(2-cyclohexanoyl)propionate was mixed with 2.1 g of a catalyst comprising active carbon and 5% by weight of palladium supported thereon (the catalyst containing 50% by weight of water). The resulting mixture in the flask was stirred at a temperature of 250° C. and a stirring power of 0.11 kW/m$^3$ for 10 hours in a nitrogen atmosphere. Thereafter, the stirring power of the reaction system was raised to 1.3 kw/m$^3$ at once and the temperature of the reaction system was raised to 270° C.

over 1 hour. This reaction mixture was then kept at 270° C. for further 15 hours while being stirred at a stirring power of 1.3 kW/m³.

After completion of the reactions, the reaction mixture was filtered to remove the catalyst, and the filtrate was analyzed by gas chromatography. As a result, it was found that the conversion of the methyl 3-(2-cyclohexanoyl)propionate was 99.98% and the yields of coumarin and 3,4-dihydrocoumarin based on the methyl 3-(2-cyclohexanoyl)propionate were 31.0% and 39.2%, respectively. That is the conversion of the methyl 3-(2-cyclohexanoyl)propionate and the yield of coumarin were sufficiently high.

EXAMPLE 2

The same procedures as in Example 1 were conducted except that the catalyst was used after being washed with water. As a result, the conversion of the methyl 3-(2-cyclohexanoyl)propionate was 100.00% and the yields of coumarin and 3,4-dihydrocoumarin based on the methyl 3-(2-cyclohexanoyl)propionate were 36.2% and 36.8%, respectively. That is, both the conversion of the methyl 3-(2-cyclohexanoyl)propionate and the yield of coumarin were sufficiently high.

EXAMPLE 3

In a 1-liter four-necked flask, 600 g of methyl 3-(2-cyclohexanoyl)propionate was mixed with 4.2 g of a catalyst comprising active carbon and 5% by weight of palladium supported thereon. The resulting mixture in the flask was stirred at a temperature of 250° C. and a stirring power of 0.11 kW/m³ for 10 hours in a nitrogen atmosphere. Thereafter, the temperature of the reaction system was raised to 270° C. over 1 hour. This reaction mixture was then kept at 270° C. for further 15 hours while being stirred at a stirring power of 0.11 kW/m³.

After completion of the reactions, the reaction mixture was filtered to remove the catalyst, and the filtrate was analyzed by gas chromatography. As a result, it was found that the conversion of the methyl 3-(2-cyclohexanoyl)-propionate was 99.97% and the yields of coumarin and 3,4-dihydrocoumarin based on the methyl 3-(2-cyclohexanoyl)propionate were 23.6% and 41.4%, respectively. That is the conversion of the methyl 3-(2-cyclohexanoyl)propionate and the yield of coumarin were sufficiently high.

COMPARATIVE EXAMPLE 1

In a 1-liter four-necked flask, 300 g of methyl 3-(2-cyclohexanoyl)propionate was mixed with 2.1 g of a catalyst comprising active carbon and 5% by weight of palladium supported thereon. The resulting mixture in the flask was stirred at a temperature of 240° C. and a stirring power of 0.11 kW/m³ for 26 hours in a nitrogen atmosphere.

After completion of the reactions, the reaction mixture was filtered to remove the catalyst, and the filtrate was analyzed by gas chromatography. As a result, it was found that the conversion of the methyl 3-(2-cyclohexanoyl)propionate was 99.87% and the yields of coumarin and 3,4-dihydrocoumarin based on the methyl 3-(2-cyclohexanoyl)propionate were 9.1% and 58.5%, respectively. That is conversion of the methyl 3-(2-cyclohexanoyl)propionate was sufficiently high, but the yield of coumarin was insufficient.

COMPARATIVE EXAMPLE 2

The reaction of methyl 3-(2-cyclohexanoyl)propionate was conducted at a constant temperature and constant stirring power in the same manner as in Comparative Example 1 except that each of various combinations of temperature and stirring power was used as shown in Table 1.

The results obtained are summarized in Table 1.

TABLE 1

| Sample No. | Temperature (°C.) | Stirring power (kW/m³) | Conversion of methyl 3-(2-cyclohexanoyl)-propionate (%) | Yield of coumarin (%) | Yield of 3,4-dichlorocoumarin (%) |
|---|---|---|---|---|---|
| 1 | 275 | 2.1 | 99.32 | 33.8 | 42.1 |
| 2 | 270 | 0.11 | 99.15 | 23.0 | 50.6 |
| 3 | 270 | 1.3 | 99.30 | 32.1 | 38.9 |
| 4 | 250 | 0.11 | 99.99 | 13.0 | 59.7 |
| 5 | 260 | 0.11 | 99.93 | 18.1 | 52.2 |

The conversions of methyl 3-(2-cyclohexanoyl)propionate in Sample Nos. 1 to 3 were insufficient. In Sample Nos. 4 and 5, the conversions of methyl 3-(2-cyclohexanoyl)propionate were sufficiently high, but the yields of coumarin were insufficient.

While the invention has been described in detail and with reference to specific embodiments thereof, it will be apparent to one skilled in the art that various changes and modifications can be made therein without departing from the spirit and scope thereof.

What is claimed is:

1. A process for producing coumarin and a derivative thereof represented by formula (2):

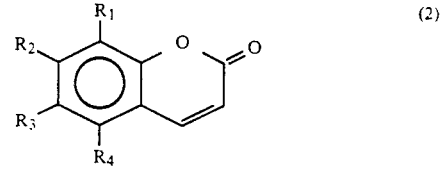

(2)

wherein R₁ to R₄ each represents a hydrogen atom, a methyl group, or an ethyl group, provided that at least two of R₁ to R₄ each represents a hydrogen atom, said process comprising the step of heating a 3-(2-cyclohexanoyl)propionic acid ester represented by formula (1):

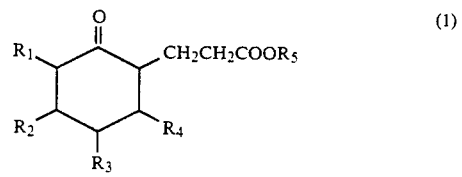

(1)

wherein R₁ to R₄ are as defined above and R₅ represents an alkyl group having from 1 to 4 carbon atoms, in the presence of a palladium catalyst, at a temperature of from 230° to 260° C. in a first stage to allow the ester of formula (1) to undergo cyclization and dehydrogenation reactions, and in a second stage of said reactions in which the conversation of the 3-(2-cyclohexanoyl) propionic acid ester used as the starting material has reached 80% or more, the temperature is higher by from 20° to 40° C. in the second stage than in the first stage of said reactions.

2. A process as claimed in claim 1, wherein the temperature for the first stage of the reactions is from 230° to 260° C. and the temperature for the second stage of the reactions is higher by from 20° to 40° C. than that for the first stage of the reactions, and the reaction system is kept being stirred at a stirring power of from 1 to 3 kW/m$^3$ throughout the first and second stage of the reactions.

3. A process as claimed in claim 1, wherein the first stage of the reactions is conducted at a temperature of from 230° to 260° C. while the reaction system is kept being stirred at a stirring power of from 0.05 to 0.5 kW/m$^3$, and the second stage of the reactions is conducted at a temperature higher by from 20° to 40° C. than that for the first stage of the reactions while the reaction system is kept being stirred at a stirring power higher by from 1 to 1.5 kW/m$^3$ than that for the first stage of the reactions.

4. A process as claimed in claim 1, wherein said palladium catalyst is used in an amount of from 0.1 to 5% by weight based on the amount of the 3-(2-cyclohexanoyl)-propionic acid ester used.

5. A process as claimed in claim 1, wherein said 3-(2-cyclohexanoyl)propionic acid ester is methyl 3-(2-cyclohexanoyl)propionate.

* * * * *